United States Patent
Kanesaka et al.

[11] Patent Number: 6,096,072
[45] Date of Patent: Aug. 1, 2000

[54] SELF-EXCHANGE STENT WITH EFFECTIVE SUPPORTING ABILITY

[75] Inventors: Nozomu Kanesaka; George A. Tashji, both of Hillsdale, N.J.

[73] Assignee: Uni-Cath Inc., N.J.

[21] Appl. No.: 09/237,367

[22] Filed: Jan. 26, 1999

[51] Int. Cl.[7] ................................................ A61F 2/06
[52] U.S. Cl. ............................................... 623/1.15
[58] Field of Search ................ 623/1, 12, 1.15, 623/1.16, 1.17, 1.18, 1.2

[56] References Cited

U.S. PATENT DOCUMENTS

| | | |
|---|---|---|
| 5,135,536 | 8/1992 | Hillstead . |
| 5,397,355 | 3/1995 | Marin et al. ................ 623/1 |
| 5,527,354 | 6/1996 | Fontaine et al. ............ 623/1 |
| 5,540,713 | 7/1996 | Schnepp-Pesch et al. . |
| 5,776,161 | 7/1998 | Globerman .................. 623/1 |
| 5,879,381 | 3/1999 | Moriuchi et al. ............ 623/1 |

FOREIGN PATENT DOCUMENTS

WO94/17754  8/1994  WIPO .

*Primary Examiner*—David H. Willse
*Assistant Examiner*—Suzette J. Jackson
*Attorney, Agent, or Firm*—Kanesaka & Takeuchi

[57] ABSTRACT

An expandable stent is formed of a plurality of rows of circularly arranged annular members situated side by side in one direction, and connecting rods for connecting the annular members together. The annular members in one row is formed substantially independently, preferably spaced apart from each other. The stent is delivered in a compressed condition in a hole, such as blood vessel, and the compressed stent is substantially fully returned to the original shape when the compressed condition is removed. The stent withstand a high compression force.

13 Claims, 4 Drawing Sheets

SELF-EXCHANGE STENT WITH EFFECTIVE SUPPORTING ABILITY

BACKGROUND OF THE INVENTION AND RELATED ART STATEMENT

The present invention relates to a self-expandable stent with effective supporting ability, which can be compressed when it is delivered and can expand automatically after it is delivered.

"Stent" is known in the art as a prosthesis or graft used for reinforcing the blood vessel, such as an artery, or for maintaining patency of a hole, such as trachea and urinary esophagus, and the blood vessel after opening a stenosis in the artery. The stent has been effectively used in the vascular treatment in place of surgical exposing, incising, removing, replacing or bypassing a defected blood vessel required in the conventional vascular surgery.

The stent has a cylindrical shape, and functions to support a part of the patient's blood vessel or another anatomical lumen from the inside thereof so as to maintain the patency of the artery or to reinforce a dissected arterial wall or like, which may impede a fluid passageway by collapse thereof. According to the clinical data, it has been reported that occurrence of re-stenosis can be greatly reduced by using the stent after opening the stenosis by the balloon catheter.

There are many kinds of stents known already in the art, which are classified into various types. In these stents, there are a self-expandable type and a balloon expandable type.

In the balloon expandable type, the stent in a closed condition is mounted on a balloon catheter, and is delivered to a lesion or stenosis through the patient's meandering artery over a guide wire preliminary introduced in the artery. After delivery of the stent to a proper position, the stent is expanded by the balloon catheter.

In the self-expandable type of the stent, the stent in a closed condition is attached to a delivery catheter, and is delivered to a lesion or stenosis through the patient's artery, similar to the balloon expandable type. After delivery of the stent to a proper position, the stent is expanded automatically, which may be made by releasing a structure for allowing the stent in the closed condition, or other mechanism, such as using a memory alloy.

In any type, the stent should be flexible to be delivered through the narrow and meandering artery. Also, the stent in the installed condition should have enough strength to sufficiently support the dissected arterial wall or to keep opening stenosis. Therefore, the stent should be flexible, has a sufficient support structure, and can expand to a large size or diameter.

In the balloon expandable type, such as U.S. Pat. No. 5,135,536 and PCT Publication No. WO 94/17754, the stent is made flexible, and expandable to have a large diameter by inflating the balloon. Especially, when a wire is bent in a zigzag shape along the outer surface of the stent, as shown in U.S. Pat. No. 5,135,536, the stent becomes flexible. However, after the stent is expanded, the expanded stent is liable to shrink again, or is easily pushed back by the force of the blood vessel applied thereto.

In the self expandable type, such as U.S. Pat. No. 5,540,713, the stent made of a memory alloy has openings in a diamond shape in its open condition. When the stent is opened, the diamond shape frame can provide scuffling structure to sufficiently support the radial force. However, because of the diamond shape frame, the stent does not have flexibility in the longitudinal direction. Therefore, the stent can not be delivered to a narrow and meandering artery.

The present invention has been made in view of the conventional stents, and an object of the invention is to provide a self expandable type flexible stent which can be easily delivered through the meandering and narrow artery.

Another object of the invention is to provide the flexible stent as stated above, which can sufficiently expand in the radial direction by its own force, and can properly support a dissected artery.

A further object of the invention is to provide the flexible stent as stated above, wherein the size of the stent after enlargement is not substantially changed or reduced.

Further objects and advantages of the invention will be apparent from the following description of the invention.

SUMMARY OF THE INVENTION

A self-expandable stent of the invention is formed of a plurality of rows of circularly arranged annular members situated side by side in one direction, i.e. longitudinal direction of the stent, and connecting rods for connecting the annular members together. The annular members in one row are formed substantially independently.

The stent formed of the annular members and the connecting rods of the invention has resiliency in the radial direction, but can withstand a relatively high radial force in an expanded condition.

The stent may be formed of a cylindrical resilient metal member, wherein the annular members and the connecting rods are cut in the final form or expanded condition. On the other hand, a cylindrical metal member may be cut in a compressed form and is expanded in the final expanded shape, which is then processed to have resiliency. In any case, the stent is formed in the expanded form, wherein the stent has resiliency in the radial direction.

When the stent is used, the stent is compressed in the radial direction to have a small diameter. The stent may be disposed in a small diameter tube or held in the compressed condition by a string or band. In the compressed condition, the stent is delivered into a hollow space, such as blood vessel, by a delivering member, such as catheter. In an appropriate position in the hollow space, the small diameter tube or band is removed from the stent, so that the compressed stent is expanded or recovered into the final shape as made.

Preferably, the annular members in one row is spaced for a predetermined distance apart from each other, and each of the annular members in one row is disposed between two of the annular members in another row situated adjacent thereto. Namely, the annular members in one row are arranged with the annular members in the adjacent row to have a staggered relation. Preferably, a part of each annular member in one row is disposed in a space between two annular members in the adjacent row, respectively, and one annular member includes four connecting rods to connect one annular member to four annular members adjacent thereto.

Preferably, the annular member has a circular shape. However, the annular member may have an oval shape. In any situation, the annular member should be all formed of curved parts, so that when the stent is compressed to have a small diameter in delivering the stent to an appropriate portion in the hollow space, the annular members can deform by using all the parts thereof. Therefore, the annular members can be properly deformed with resiliency. Also, when the compression force to the stent is removed in the hollow space, the shape of the stent can be fully recovered.

Further, when a compression force or pressure is applied to the stent in the hollow space after delivery, the pressure is distributed to substantially all the parts of the annular members. Thus, the stent does not substantially shrink or is not pushed back after delivery, and can withstand the large radial force applied thereto.

The connecting rods may be formed of a plurality of first connecting rods situated at longitudinal ends of the stent, and a plurality of second connecting rods. Each first connecting rod connects two of the annular members disposed in one row of the annular members at the longitudinal end of the stent. Each second connecting rod connects one annular member in one row to another annular member in another row adjacent thereto. In a middle of the stent, one annular member in one row is connected to two annular members in an adjacent row at one side thereof, and to two annular members in an adjacent row at the other side thereof.

The second connecting rod extends substantially linearly between two annular members. Preferably, the second connecting rod between two annular members is arranged tangential to the two annular members. This arrangement helps deformation of the annular members without any partial stress, so that the annular members can be deformed smoothly when high pressure is applied to compress the stent, and the annular members can smoothly recover their shapes when the pressure is removed.

The first connecting rod includes two substantially linear sections and one curved section between the two linear sections. The first connecting rod has a shape substantially symmetrical to a shape of two second connecting rods and a part of the annular member sandwiched therebetween with respect to a plane extending through centers of the circularly arranged annular members located at an end of the stent.

DETAILED DESCRIPTION OF THE PREFERRED EMBODIMENTS

Figure 1:
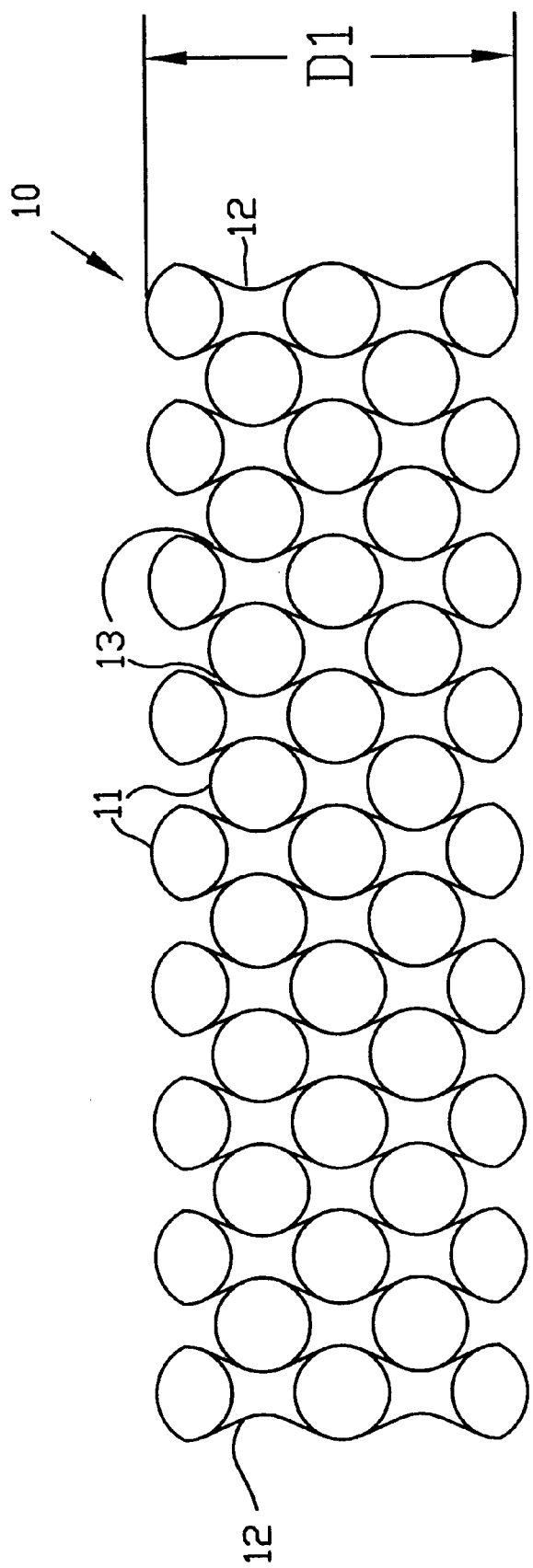
FIG. 1 is an explanatory side view of a stent in an expanded condition according to the present invention.

The invention will be explained with reference to the accompanying drawings.

The stent 10 of the invention is formed of a plurality of annular members 11, and first and second connecting rods 12, 13 for connecting the annular members 11 together. The first connecting rods 12 are arranged at the longitudinal ends of the stent, and the second connecting rods 13 are used for other portions.

The annular members 11 are arranged circularly to form a row of the circularly arranged annular members 11 spaced apart from each other in the circumferential direction, and the rows of the circularly arranged annular members 11 are disposed side by side with a space therebetween along a longitudinal direction of the stent. One annular member 11 in one row is partly located in a space between two annular members 11 in the adjacent row of the annular members 11. Thus, the annular members are arranged in a staggered relationship.

Each of the annular members 11 situated in the middle of the stent 10 has four second connecting rods 13 to be connected to the adjacent annular members 11. Also, each of the annular members 11 located at the longitudinal ends of the stent has two first connecting rods 12 and two second connecting rods 13.

Figure 5:
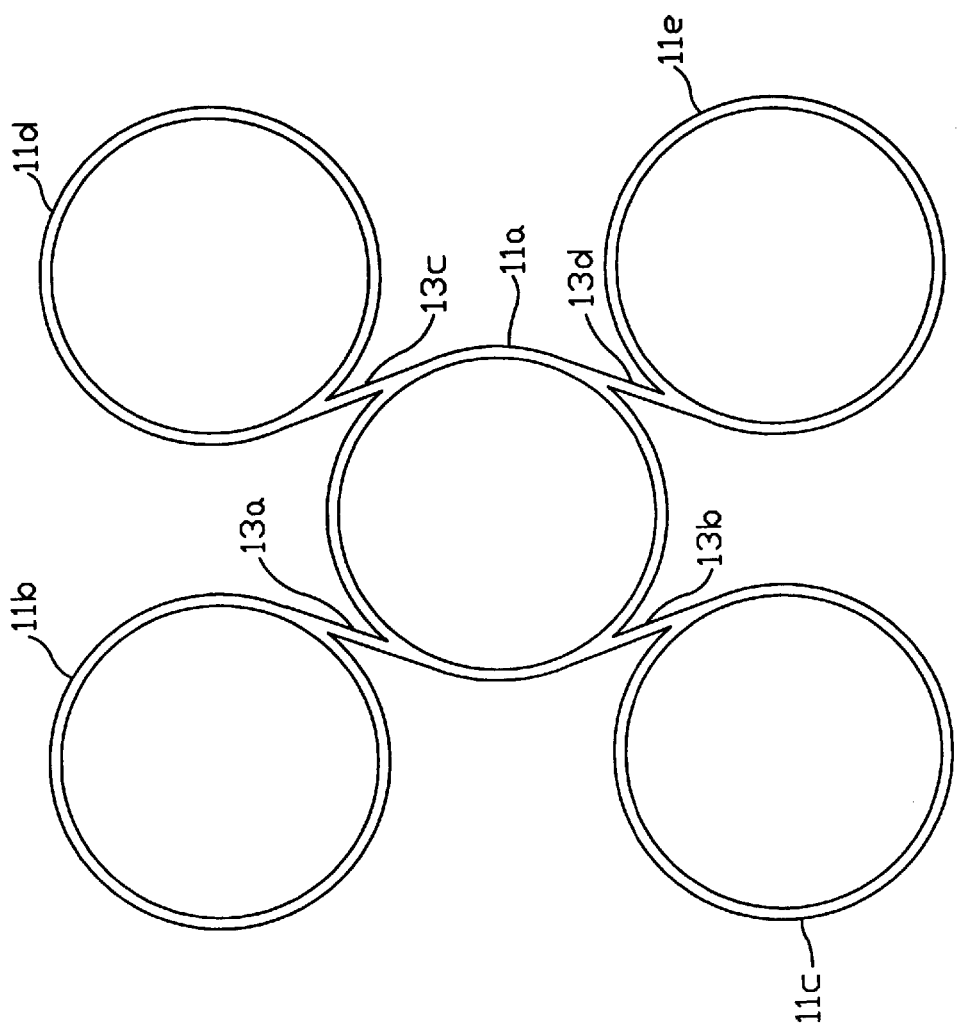
FIG. 5 is an enlarged explanatory side view of a part of the stent in the expanded condition.

FIG. 5 shows the connections of five annular members 11a–11e in the stent 10, as an example. In the complete form of the stent 10, the annular members 11a–11e as shown in FIG. 5 are connected to form the cylindrical shape together with other annular members. Namely, one annular member 11a located in one row of the circularly arranged annular members is connected to the annular members 11b, 11c located at a left side row of the circularly arranged annular members by second connecting rods 13a, 13b, and to the annular members 11d, 11e located at a right side row of the circularly arranged annular members by second connecting rods 13c, 13d.

The second connecting rods 13 (13a–13d) are substantially straight though they are curved slightly along the circumferential direction of the stent. The second connecting rods 13 are arranged tangential to the annular members 11 (11a–11e) connected thereto, and are slightly inclined in the longitudinal direction of the stent. Namely, in regard to the annular member 11a, the distance between the outer ends of the second connecting rods 13a, 13c, where the second connecting rods 13a, 13c are connected to the annular members 11b, 11d, is shorter than that between the bottom ends thereof where the second connecting rods 13a, 13c are connected to the annular member 11a.

Since the second connecting rods 13 are inclined as stated above, the stent 10 has a flexibility along the longitudinal direction of the stent 10. Thus, when the stent 10 is delivered to the proper position in the blood vessel, the stent 10 can be bent relatively easily to provide easy installation or delivery of the stent.

Each of the first connecting rods 12 located at the longitudinal ends of the stent 10 connects two annular members 11 in the end row of the stent. The first connecting rod 12 has two straight portions 12a and a curved portion 12b between the straight portions 12a, and is arranged such that the first connecting rod 12 is symmetrical to two second connecting rods 13 and a part of the annular member 13 between the second connecting rods 13 with respect to a line passing through the centers of the annular members 13 at the end row.

Figure 2:
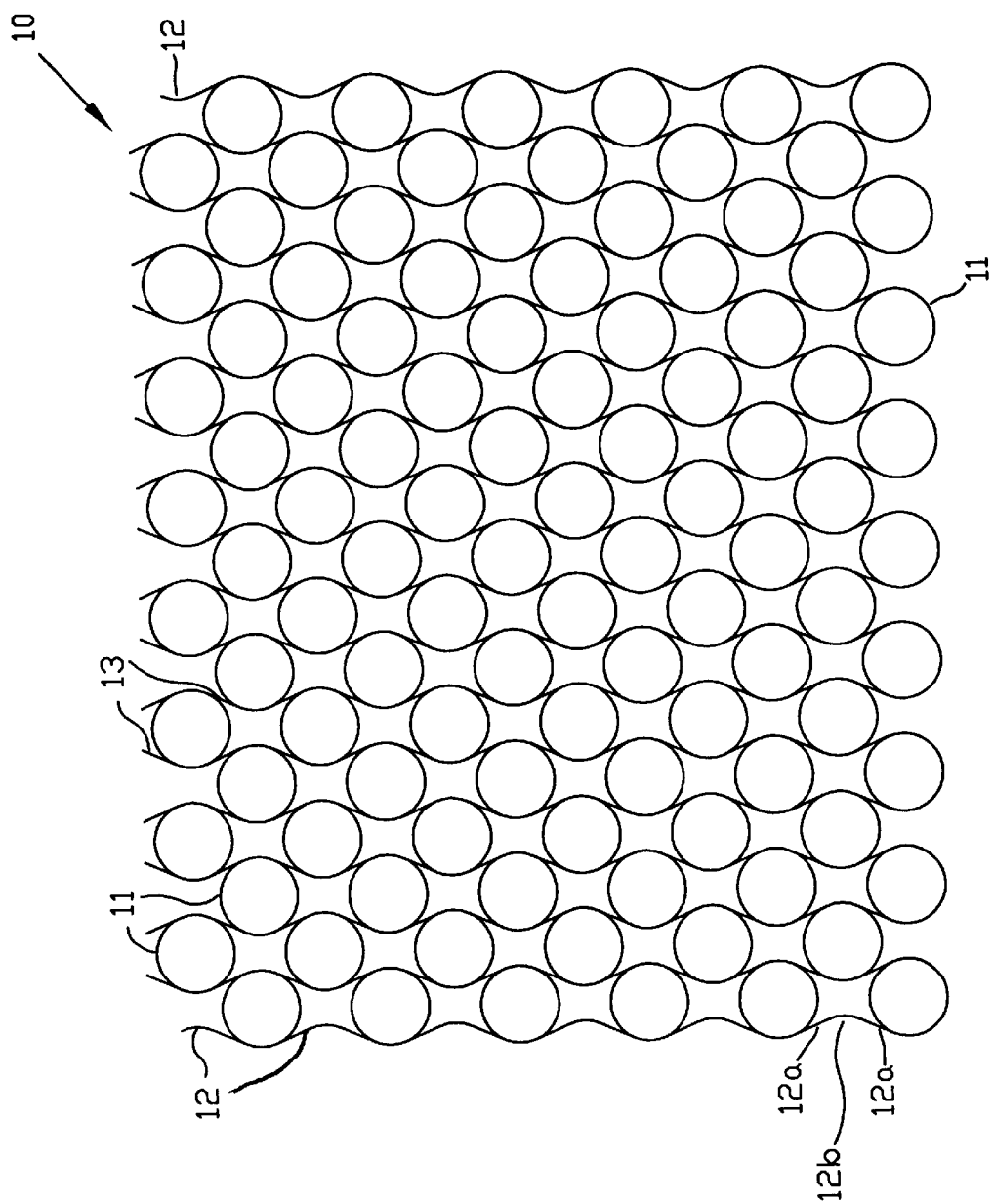
FIG. 2 is an explanatory plan view of the stent, wherein the stent is shown in a flat sheet form.
Figure 3:
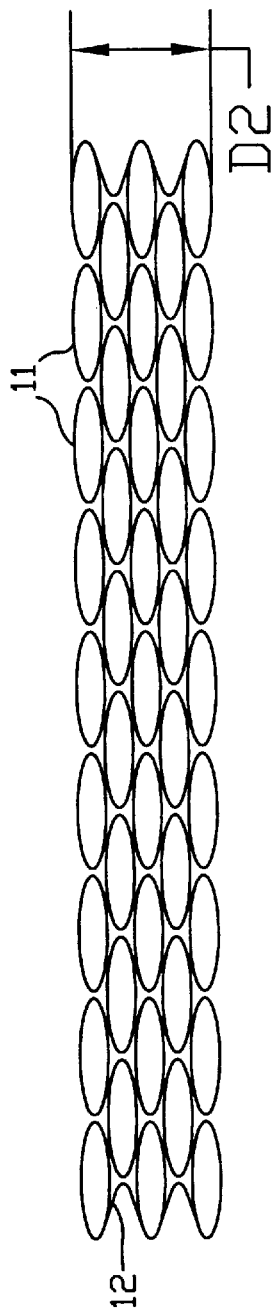
FIG. 3 is an explanatory side view of the stent in a compressed condition.

As shown in FIGS. 1, 2 and 5, the annular member 11 has a circular shape, but the annular member 11 may have an oval shape, such as shown in FIG. 3 as the compressed condition. In the stent of the invention, the annular member 11 must be all formed of curved portions, not a combination of a straight portion and a curved portion, to have a sufficient recovery force when it is compressed and to withstand a high compression force when it is disposed in the blood vessel in use.

The stent 10 is formed by cutting holes in a cylindrical metal member to have the annular members 11 and the first and second connecting rods 12, 13 by means of etching, laser beam, and so on. The cutting of the metal member may be made in the final or expanded shape. In this case, the metal member may have resiliency, or after cutting, the metal member may be processed to have resiliency. In case the cutting is made in a slightly compressed shape, e.g. relatively flattened oval shape, after cutting, the stent is enlarged into the expanded shape, which is then processed to have resiliency.

Figure 4:
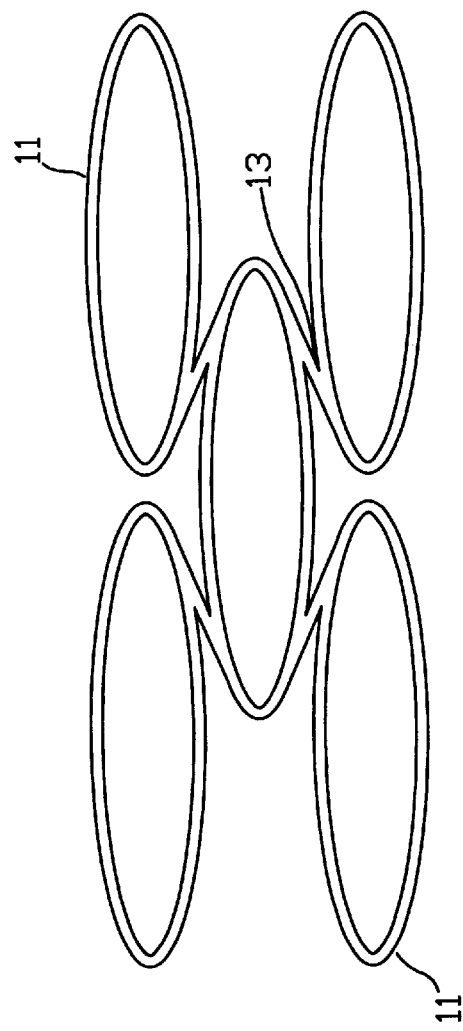
FIG. 4 is an enlarged explanatory side view of a part of the stent in the compressed condition.

When the stent 10 thus formed is used, the stent 10 with a diameter $D_1$ as shown in FIG. 1 is compressed to have a shape with a diameter $D_2$ as shown in FIG. 3. In the compressed condition, as shown in FIG. 4, the circular annular members 11 are flattened in the oval shape, but the second connecting rods 13 are not substantially bent. Namely, the bending force applied to the stent 10 is mostly applied to the annular members 11 with the circular shape. Since the bending force is spread to all the parts of the annular members, not concentrated in specific portions of the annular members in the stent, the resiliency is retained substantially completely in the annular members 11 of the stent 10.

The compressed stent 10 is retained in a tube (not shown), or is held in the compressed condition by a string or band (not shown). The compressed stent 10 is attached to a delivery device, such as catheter (not shown), and is delivered to a proper portion in a hollow space, such as blood vessel. Then, the tube, string or band covering the stent 10 is removed by the delivery device, wire or other mechanism, so that the compressed stent 10 returns to the original shape before it is compressed. Namely, the stent 10 automatically opens to the original shape with the diameter $D_1$. Generally, the diameter $D_1$ is greater in about 20% than the diameter $D_2$.

In the invention, when the annular members 11 are compressed into the oval shape, the resiliency is spread generally equally in the annular members 11, so that when the tube is removed from the compressed annular members, the annular members 11 substantially completely return to the original shapes. Since there is no specific bending portion in the stent, the stent can recover its shape substantially completely.

In the invention, the second connecting rods are attached tangentially to the annular members and inclined on the surface of the stent with respect to a line perpendicular to the longitudinal direction of the stent. Therefore, when the annular members are compressed, the second connecting rods help compressing the annular members. On the other hand, when the compressed annular members are returned to the original shapes, the second connecting rods help returning the annular members to the original shapes. Further, the above arrangements of the second connecting rods provide flexibility to the stent in the axial direction.

In the above embodiment, the annular members are spaced for a predetermined distance apart from each other in the circumferential direction and are arranged in a staggered relationship. However, the circularly arranged annular members in one row may be disposed close to each other without a substantial space therebetween, and two annular members in one row may be connected together at one portion. The annular members in one row are disposed next to the annular members in the next row so that the annular members are low arranged in the longitudinal direction of the stent without forming a staggered relationship. Some of the annular members in one row are connected to the adjacent annular members in the next row by the connecting rods to provide flexibility in the longitudinal direction.

In the invention, when the radial force is applied to the stent in use, such a radial force is applied to all the parts of the annular members. Thus, the stent is not substantially pushed back or does not reduce its size in use. The stent can withstand relatively high radial force.

While the invention has been explained with reference to the specific embodiments of the invention, the explanation is illustrative and the invention is limited only by the appended claims.

What is claimed is:

1. A self-expandable stent, comprising:

a plurality of rows of circularly arranged annular members situated side by side in one direction, said annular members in one row being formed substantially independently and spaced for a predetermined distance away from each other so that each of the annular members in one row is disposed between two of the annular members in another row situated adjacent thereto and between two of the annular members in the other row situated at a side opposite to said another row relative to said one row, and connecting rods for connecting the annular members together, four connecting rods extending from one annular member to connect said one annular member to four annular members adjacent thereto so that two out of the four connecting rods being connected to said two of the annular members in said another row and the other two out of the four connecting rods being connected to said two of the annular members in said other row.

2. A self-expandable stent according to claim 1, wherein said connecting rods include a plurality of first connecting rods situated at longitudinal ends of the stent, each first connecting rod connecting two of the annular members disposed in one row of the annular members, and a plurality of second connecting rods, each second connecting rod connecting one annular member in one row to another annular member in a different row adjacent thereto.

3. A self-expandable stent according to claim 2, wherein said second connecting rod extends substantially linearly between two annular members.

4. A self-expandable stent according to claim 3, wherein said second connecting rod between two annular members is arranged tangential to the two annular members.

5. A self expandable stent according to claim 2, wherein said first connecting rod includes two substantially linear sections and one curved section between the two linear sections so that the first connecting rod has a shape substantially symmetrical to a shape of two second connecting rods and a part of the annular member sandwiched therebetween with respect to a plane extending through centers of the circularly arranged annular members located at an end of the stent.

6. A self-expandable stent according to claim 1, wherein said annular member has a circular shape.

7. A self-expandable stent according to claim 1, wherein said annular member has an oval shape.

8. A self-expandable stent according to claim 1, wherein said annular members in one row are arranged relative to the annular members in an adjacent row so that a part of each annular member in said one row is located in a space between two annular members in said adjacent row, respectively.

9. A self-expandable stent according to claim 8, wherein said annular members and said connecting rods have resiliencies so that when the stent is subjected to a radially inward force, the annular members are deformed to have longitudinally extended shapes, which are recovered when the radially inward force applied to the stent is removed.

10. A self-expandable stent according to claim 1, wherein said four connecting rods extend substantially in a circumferential direction of the stent from said one annular member, two out of said four connecting rods forming a pair, respectively, extending in a same direction, each of said pair inclining toward a center line passing through centers of the annular members in said one row.

11. A self-expandable stent according to claim 1, wherein said one annular member with the four connecting rods is located in a middle of the stent.

12. A self-expandable stent according to claim 1, wherein said stent has an expanded condition and a compressed condition, said connecting rods being connected to the annular members such that the connecting rods are not substantially bent when the stent is compressed into the compressed condition.

13. A self-expandable stent, comprising:
- a plurality of rows of circularly arranged annular members situated side by side in one direction, said annular members in one row being formed substantially independently and spaced for a predetermined distance away from each other so that each of the annular members in one row is disposed between two of the annular members in another row situated adjacent thereto, and
- connecting rods for connecting the annular members together, said connecting rods including a plurality of first connecting rods situated at longitudinal ends of the stent, each first connecting rod connecting two of the annular members disposed in one row of the annular members, and a plurality of second connecting rods, each second connecting rod connecting one annular member in one row to another annular member in another row adjacent thereto so that four second connecting rods extend from one annular member to connect said one annular member to four annular members adjacent thereto, said first connecting rod having two substantially linear sections and one curved section between the two linear sections so that the first connecting rod has a shape substantially symmetrical to a shape of two second connecting rods and a part of the annular member sandwiched therebetween with respect to a plane extending through centers of the circularly arranged annular members located at an end of the stent.

* * * * *